United States Patent
Silverberg

(10) Patent No.: US 10,912,765 B2
(45) Date of Patent: *Feb. 9, 2021

(54) COMPOSITIONS AND METHODS FOR NON-SURGICAL TREATMENT OF PTOSIS

(71) Applicant: VOOM, LLC, Santa Barbara, CA (US)

(72) Inventor: Mark Silverberg, Santa Barbara, CA (US)

(73) Assignee: VOOM, LLC, Santa Barbara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/577,262

(22) Filed: Sep. 20, 2019

(65) Prior Publication Data

US 2020/0009114 A1 Jan. 9, 2020

Related U.S. Application Data

(63) Continuation of application No. 15/837,325, filed on Dec. 11, 2017, which is a continuation of application No. 14/625,099, filed on Feb. 18, 2015, now Pat. No. 9,867,808, which is a continuation of application No. 13/218,584, filed on Aug. 26, 2011, now abandoned.

(60) Provisional application No. 61/448,949, filed on Mar. 3, 2011.

(51) Int. Cl.
| | | |
|---|---|---|
| A61K 31/4174 | (2006.01) | |
| A61P 21/00 | (2006.01) | |
| A61P 27/02 | (2006.01) | |
| A61K 9/00 | (2006.01) | |
| A61K 31/4164 | (2006.01) | |
| A61K 31/137 | (2006.01) | |
| A61K 31/00 | (2006.01) | |
| A61K 31/135 | (2006.01) | |
| A61P 21/04 | (2006.01) | |

(52) U.S. Cl.
CPC ........ *A61K 31/4164* (2013.01); *A61K 9/0048* (2013.01); *A61K 31/00* (2013.01); *A61K 31/135* (2013.01); *A61K 31/137* (2013.01); *A61K 31/4174* (2013.01); *A61P 21/00* (2018.01); *A61P 27/02* (2018.01); *A61P 21/04* (2018.01); *Y10S 514/912* (2013.01)

(58) Field of Classification Search
None
See application file for complete search history.

(56) References Cited

U.S. PATENT DOCUMENTS

| | | | |
|---|---|---|---|
| 3,670,087 A | 6/1972 | Lorenzetti | |
| 4,425,345 A | 1/1984 | Horlington et al. | |
| 5,459,133 A | 10/1995 | Neufeld | |
| 5,885,550 A | 3/1999 | Vallier | |
| 6,572,849 B2 | 6/2003 | Shahinian, Jr. | |
| 6,730,691 B1 | 5/2004 | Galin | |
| 6,806,364 B2 | 10/2004 | Su et al. | |
| 7,022,740 B2 | 4/2006 | Mackles | |
| 7,812,049 B2 | 10/2010 | Shanler et al. | |
| 8,357,714 B2 | 1/2013 | Silverberg | |
| 8,420,688 B2 | 4/2013 | Shanler et al. | |
| 8,685,439 B2 | 4/2014 | Chapin et al. | |
| 8,709,508 B2 | 4/2014 | Jones et al. | |
| 8,758,816 B2 | 6/2014 | Fuge et al. | |
| 8,815,929 B2 | 8/2014 | Shanler et al. | |
| 8,883,838 B2 | 11/2014 | Shanler et al. | |
| 9,011,941 B2 | 4/2015 | Jones et al. | |
| 9,018,240 B2 | 4/2015 | Silverberg | |
| 9,867,808 B2 | 1/2018 | Silverberg | |
| 9,974,773 B2 | 5/2018 | Sarpotdar et al. | |
| 2002/0037297 A1 | 3/2002 | Crespo et al. | |
| 2005/0245484 A1 | 11/2005 | Mackles | |
| 2006/0127446 A1 | 6/2006 | Van Dalen | |
| 2006/0177430 A1 | 8/2006 | Bhushan et al. | |
| 2007/0264318 A1 | 11/2007 | Chapin et al. | |
| 2010/0173019 A1 | 7/2010 | Paik et al. | |
| 2010/0240625 A1 | 9/2010 | Abelson et al. | |
| 2010/0311688 A1 | 12/2010 | Chapin et al. | |
| 2012/0225918 A1 | 9/2012 | Silverberg | |

(Continued)

FOREIGN PATENT DOCUMENTS

| | | |
|---|---|---|
| CN | 101977595 A | 2/2011 |
| DE | 3227741 A1 | 1/1984 |

(Continued)

OTHER PUBLICATIONS

Brar et al., Blepharochalasis—A rare entity, 2008, Dermatology Online Journal, vol. 14, Issue 1, Retrieved from https://escholarship.org/uc/item/14g254jd, 3 pages.*

Breakey, A. S. et al., "A double-blind, multi-centre controlled trial of 0.025% oxymetazoline ophthalmic solution in patients with allergic and non-infectious conjunctivitis" *Pharmatherapeutica*, 2(6):353-356 (USA, 1980).

Chu et al., "Oxymetazoline: potential mechanisms of inhibitory effects on aqueous humor dynamics," Pharmacology, 53(4): 259-270 (1996).

Duzman, E. et al., "Efficacy and Safety of Topical Oxymetazoline in Treating Allergic and Environmental Conjunctivitis", *Ann. Ophthalmol.*, 18:28-31 (1986).

Duzman, E. et al., "Topically Applied Oxymetazoline: Ocular Vasoconstrictive Activity, Pharmacokinetics, and Metabolism", *Arch. Ophthalmol.*, 101:1122-1126 (1983).

(Continued)

*Primary Examiner* — Gigi G Huang
(74) *Attorney, Agent, or Firm* — Foley Hoag LLP

(57) ABSTRACT

Provided are pharmaceutical compositions, and methods of use of the compositions, for the non-surgical treatment of ptosis (eyelid droop). In one embodiment the composition includes oxymetazoline 0.1% formulated for topical administration to an eye. In one embodiment the composition includes a synergistic combination of oxymetazoline and phenylephrine, formulated for topical administration to an eye. Oxymetazoline alone causes no pupillary dilation (mydriasis), and a synergistic combination of oxymetazoline and phenylephrine induces no clinically significant mydriasis. In addition to providing desirable cosmetic effects, the compositions and methods of the invention can improve visual fields otherwise compromised by ptosis.

9 Claims, 5 Drawing Sheets

(56) References Cited

U.S. PATENT DOCUMENTS

| | | |
|---|---|---|
| 2012/0225920 A1 | 9/2012 | Silverberg |
| 2014/0161903 A1 | 6/2014 | Chapin et al. |
| 2016/0038465 A1 | 2/2016 | Silverberg |
| 2018/0050026 A1 | 2/2018 | Mahadevan et al. |
| 2018/0071390 A1 | 3/2018 | Patel et al. |
| 2018/0147214 A1 | 5/2018 | Ostrow et al. |
| 2018/0263962 A1 | 9/2018 | Sarpotdar et al. |
| 2018/0325806 A1 | 11/2018 | Litvack et al. |
| 2018/0338953 A1 | 11/2018 | Silverberg |
| 2018/0360827 A1 | 12/2018 | Shanler et al. |
| 2019/0008857 A1 | 1/2019 | Shanler et al. |
| 2020/0009114 A1 | 1/2020 | Silverberg |

FOREIGN PATENT DOCUMENTS

| | | |
|---|---|---|
| JP | 2006-213700 A | 8/2006 |
| JP | 2011-503061 A | 1/2011 |
| WO | WO-98/47510 A1 | 10/1998 |
| WO | WO-2007/127333 A2 | 11/2007 |
| WO | WO-2012/017077 A1 | 2/2012 |

OTHER PUBLICATIONS

Flach, A. J. et al., "Ptosis in the Rat Following Topically Administered 2% Epinephrine", Investigative Ophthalmology and Visual Science, 24(6):766-771 (Association for Research in Vision and Ophthalmology, USA, 1983).

Fox, S. L. et al., "Oxymetazoline in the Treatment of Allergic and Non-Infectious Conjunctivitis", J. Int. Med. Res., 7:528-530 (1979).

Garibaldi, et al., "Effect of 0.5% apraclonidine on ptosis in Horner syndrome," Ophthal Plast Reconstr Surg, 22(1): 53-55 (2006).

Glatt, et al., "Comparison of 2.5% and 10% phenylephrine in the elevation of upper eyelids with ptosis", Ophthalmic Surg., 21(3):173-176 (1990).

Houben, et al., "A novel approach to the study of human microcirculation: Reactivity to the locally applied angiotensin Ii in the conjunctival microvascular bed," J Hypertens, 24(11): 2225-2230 (2006).

International Search Report from corresponding PCT application PCT/US2012/026496 dated May 10, 2012.

Kusumoto, et al., "Etiology and classification of blepharoptosis," Japanese Journal of Plastic Surgery, 53(1): 5-13 (2010).

Lee, M. S. et al., "Patient Use of Visine (tetrahydrozoline) masks Horner syndrome", British Journal of Ophthalmology, 92(1):149-150 (UK, Jan. 2008).

Machata, A.-M. et al., "Awake Nasotracheal Fiberoptic Intubation: Patient Comfort, Intubating Conditions, and Hemodynamic Stability During Conscious Sedation with Remifentanil", Anesthesia and Analgesia, 97(3):904-908 (USA, Sep. 1 2003).

Megens, A. A. H. P. et al., "Further validation of in vivo and in vitro pharmacological procedures for assessing the $\alpha_2/\alpha_1$-selectivity of test compounds: (2) $\alpha$-adrenoceptor agonists", European Journal of Pharmacology, 129(1-2):57-64 (Elsevier; Beerse,Belgium; Sep. 23, 1986).

Mindel, "Alpha-Adrenergic Drugs—Drug effect on Adrenergic Function," Duane's Ophthalmology, 3(29); retrieved from <http://www.oculist.net/downaton502/prof/ebook/duanes/pages/v9/v9c029.html>.

Munden, et al., "Palpebral fissure responses to topical adrenergic drugs," Am J Ophthalmol, 111(6): 706-710 (1991).

Non-Final Office Action for U.S. Appl. No. 13/218,584 dated Feb. 6, 2014.

Reifen, "Vitamin A as an anti-inflammatory agent," PNAS, 61(3): 397-400 (2002).

Samson, C. R. et al., "Safety and toleration of oxymetazoline ophthalmic solution", Pharmatherapeutica, 2(6):347-352 (USA, 1980).

Scheinfeld, N., M.D., "The Use of Apraclonidine Eyedrops to Treat Ptosis After the Administration of Botulinum Toxin to the Upper Face", Dermatology Online Journal, 11(1):9 (NYC, USA, 2005).

U.S. Pharmacopeia, "Oxymetazoline Hydrochloride Ophthalmic Solution," https://ftp.uspbpep.com/v29240/usp29nf24s0_m59635.html, (2007).

Vajpayee, R. B. et al., "Management of benign red eye (evaluation of topical oxymetazoline—a double masked study)", Indian J. Ophthalmol., 34:33-36 (1986).

Written Opinion from corresponding PCT application PCT/US2012/026496 dated May 10, 2012.

Xuan, B. et al., "Efficacy of Oxymetazoline Eye Drops in Non-Infectious Conjunctivitis, the Most Common Cause of Acute Red Eyes", J. Ocul. Pharmacol. Ther., 13(4):363-367 (USA, 1997).

Yazici, B. et al., "Use of 0.5% apraclonidine solution in evaluation of blepharoptosis", Ophthalmic Plastic and Reconstructive Surgery, 24(4):299-301 (Lippincott Williams and Wilkins, USA, Jul. 2008).

"Child-proof closures for ophthalmic packaging," https://www.eppm.com/materials/child-proof-closures-for-ophthalmic-packaging/, European Plastic Product Manufacturer ("EPPM"), Oct. 27, 2015.

Anderson et al., "The levator aponeurosis," Arch Ophthalmol, 95:1437-1441 (1977).

Beard et al., "Muller's superior tarsal muscle: Anatomy physiology, and clinical significance," Annals of Plastic Surgery, 14(4):324-333 (1985).

Cannady et al., "Comparison of Delivery of Topical Medications to the Paranasal Sinuses via "Vertex-to-floor" Position and Atomizer Spray after FESS," Otolaryngology-Head and Neck Surgery, 133(5): 735-740 (2005).

Custer, "Blepharoptosis," Ophthalmology, 3rd Edition, 1397-1403 (2009).

Finsterer, "Ptosis: causes, presentation, and management," Aesthetic Plast Surg, 27(3):193-204 (2003).

Fraunfelder et al., "Possible adverse effects from topical ocular 10% phenylephrine," Am J Ophthalmol, 85(4):447-453 (1978).

Garcia-Campana et al., "Flow injection analysis of oxymetazoline hydrochloride with inhibited chemiluminescent detection," Analytica Chemica Acta, 516:245-249 (2004).

Hayes et al., "Rapid liquid chromatographic-mass spectrometric assay for oxymetazoline in whole rat blood," Journal of Chromatography A, 692:73-81 (1995).

Ho et al., "Modified visual field test for ptosis surgery (Leicester Peripheral Field Test," Eye, 25(3):365-369 (2011).

Jarvinen et al., "Prodrugs for improved ocular drug delivery," Advanced Drug Delivery Reviews, 19:203-224 (1996).

Kass, "Dipivefrin and epinephrine treatment of elevated intraocular pressure: a comparative study," Arch Ophthalmol, 97(10):1865-1866 (1979).

Kersten, "Acquired ptosis in the young and middle-aged adult population," Ophthalmology, 102:924-928 (1995).

Lalezary, ARVO Annual Meeting Abstract, Investigative Ophthalmology & Visual Science, vol. 50, 5048, Apr. 2009.

Matjucha, "Chapter 16: The nonsurgical treatment of ptosis," in Cohen and Weinberg, eds., Evaluation and Management of Blepharoptosis, Springer New York, 155-161 (2011).

Partial European Search Report for EP Application 19199263.5 dated Apr. 3, 2020.

Putterman et al., "Muller muscle-conjunctiva resection: Technique for Treatment of Blepharoptosis," Arch Opthalmol, 93:619-623 (1975).

Rai et al., "The suprachoroidal pathway: a new drug delivery route to the back of the eye," Drug Discovery Today, 204(4):491-495 (2014).

Reddy et al., "Ptosis in young soft contact lens wearers," Ophthalmology, 114:2730 (2007).

Schoenwald et al., "Ocular Drug Delivery: Pharmacokinetic Considerations," Clin Pharmacokinet, 18(4):225-269 (1990).

Shah-desai et al., "Scleral contact lens usage in patients with complex blepharoptosis," Ophthal Plast Reconstr Surg, 27(2):95-98 (2011).

Sherman et al., "Intrathecal oxymetazoline produces analgesia via spinal alpha-adrenoceptors and potentiates spinal morphine," European Journal of Pharmacology, 148:371-380 (1988).

Sherman et al., "Prolonged spinal analgesia in the rat with the $\alpha$-adrenoceptor agonist oxymetazoline," European Journal of Pharmacology, 140(1): 25-32 (1987).

(56) References Cited

OTHER PUBLICATIONS

Sridharan et al., "A community survey of ptosis of the eyelid and pupil size of elderly people," Age and Ageing, 24(1):21-24 (1995).
Svensson et al., "Topical vasoconstrictor (oxymetazoline) does not affect histamine-induced mucosal exudation of plasma in human nasal airways," Clinical and Experimental Allergy, 22:411-416 (1992).
Urtti et al., "Systemic absorption of ocular pilocarpine is modified by polymer matrices," International Journal of Pharmaceutics, 23:147-161 (1985).
Van Den Bosch et al., "Blepharoptosis induced by prolonged hard contact lens wear," Ophthalmology, 99:1759-1765 (1992).
Yamamoto et al., "The ocular route for systemic insulin delivery in the albino rabbit," The Journal of Pharmacology and Experimental Therapeutics, 249(1):249-255 (1989).
Extended European Search Report for EP Application No. 19199263.5 dated Jul. 23, 2020.
Lal, "Drop volume of commercial anti-glaucoma eye drops," Indian Journal of Pharmacology, 25:163-164 (1993).
Sklubalova et al., "Systematic study of factors affecting eye drop size and dosing variability," Pharmazie, 60(12):917-921 (2005).

\* cited by examiner

COMPOSITIONS AND METHODS FOR NON-SURGICAL TREATMENT OF PTOSIS

RELATED APPLICATIONS

This application is a continuation of U.S. patent application Ser. No. 15/837,325, filed Dec. 11, 2017, which is a continuation of U.S. patent application Ser. No. 14/625,099, filed Feb. 18, 2015, now U.S. Pat. No. 9,867,808, which is a continuation of U.S. patent application Ser. No. 13/218,584, filed Aug. 26, 2011, now abandoned, which claims benefit under 35 U.S.C. § 119(e) of U.S. Provisional Patent Application No. 61/448,949, filed Mar. 3, 2011. Each of these applications is incorporated by reference in its entirety.

BACKGROUND OF THE INVENTION

Ptosis is abnormal partial or complete drooping of the upper eyelid. Ptosis occurs when the muscles that raise the eyelid (levator palpebrae superioris and Müller's muscles) are not strong enough to do so properly. It can affect one eye or both eyes and is more common in the elderly, as muscles in the eyelids may begin to deteriorate. Fatigue is a common reversible cause of ptosis, giving an affected individual an appearance characterized by "tired eyes."

It is common for affected individuals to seek medical help to treat ptosis, as it creates a tired-looking appearance, thereby interfering with social relationships. In more severe cases ptosis can even interfere with vision as the upper lid partially or totally covers the pupil. While there are numerous recognized causes of ptosis, it is common to treat ptosis with ophthalmic plastic surgery. Non-surgical modalities for the treatment of ptosis include the use of "crutch" glasses or special scleral contact lenses to support the eyelid.

SUMMARY OF THE INVENTION

The invention provides compositions and methods useful in the treatment of ptosis. Compositions of the invention include an effective amount of a long-acting alpha adrenergic agonist and, optionally, a short-acting alpha adrenergic agonist. In one embodiment the compositions are formulated for topical administration to the eye. As described herein, the compositions and methods of the invention can be used to treat ptosis in a non-surgical method. The methods provide long-lasting reversible treatment for ptosis in suitable subjects.

It has been discovered, in making the instant invention, that oxymetazoline unexpectedly can be administered to an eye to treat ptosis without affecting pupil size. This observation was unexpected because oxymetazoline is an alpha adrenergic agonist, and other alpha adrenergic agonists are known commonly to cause pupillary dilation (mydriasis).

More particularly, it has been discovered that oxymetazoline, at least in the amounts and at the concentrations used in accordance with the instant invention, does not cause mydriasis. Accordingly, in certain embodiments the compositions and methods of the invention are disclosed to be useful to treat ptosis without causing mydriasis commonly obtained with alpha adrenergic agonists topically administered to the eye.

It has also been discovered, in making the instant invention, that oxymetazoline and phenylephrine unexpectedly can be used in combination to treat ptosis, with a synergistic effect. More particularly, it has been discovered that the effect on lid aperture of a combination of oxymetazoline and phenylephrine is greater than the sum of the effects of oxymetazoline alone and phenylephrine alone. Moreover, such combination can also be used to treat ptosis without causing clinically significant mydriasis.

The compositions and methods of the invention are disclosed to be useful to treat visual field defects arising from ptosis.

An aspect of the invention is a method for treating ptosis in a subject. The method includes the step of administering an effective amount of oxymetazoline to the exterior surface of an eye of a subject in need of such treatment.

In one embodiment the administering results in at least a 1 millimeter (mm) increase in the vertical separation of the upper and lower lids of the eye. In one embodiment the administering results in at least a 10 percent increase in the vertical separation of the upper and lower lids of the eye.

In one embodiment the oxymetazoline is formulated as a pharmaceutical composition comprising at least 0.05 weight percent oxymetazoline in an ophthalmologically acceptable carrier. In one embodiment the oxymetazoline is provided as a pharmaceutically acceptable salt of oxymetazoline.

In one embodiment the administering is administering as a single drop.

In one embodiment the administering is administering at least once daily. In one embodiment the administering is administering once daily.

In one embodiment the subject does not have an allergic ocular condition calling for treatment of the eye with oxymetazoline. In one embodiment the subject does not have eyelid swelling. In one embodiment the subject has not undergone refractive eye surgery.

An aspect of the invention is a method for treating ptosis in a subject. The method includes the step of administering an effective amount of a long-acting alpha adrenergic agonist and an effective amount of a short-acting alpha adrenergic agonist to the exterior surface of an eye of a subject in need of such treatment.

In one embodiment the long-acting alpha adrenergic agonist is oxymetazoline or a pharmaceutically acceptable salt thereof.

In one embodiment the short-acting alpha adrenergic agonist is phenylephrine or a pharmaceutically acceptable salt thereof.

In one embodiment the administering results in at least a 1 millimeter (mm) increase in the vertical separation of the upper and lower lids of the eye. In one embodiment the administering results in at least a 10 percent increase in the vertical separation of the upper and lower lids of the eye.

In one embodiment the oxymetazoline is formulated as a pharmaceutical composition comprising at least 0.05 weight percent oxymetazoline in an ophthalmologically acceptable carrier.

In one embodiment the long-acting alpha adrenergic agonist is provided as a pharmaceutical composition comprising at least 0.1 weight percent oxymetazoline and the short-acting alpha adrenergic agonist is provided as a pharmaceutical composition comprising at least 0.15 weight percent phenylephrine. In one embodiment the long-acting alpha adrenergic agonist is provided as a pharmaceutical composition comprising at least 0.1 weight percent oxymetazoline and the short-acting alpha adrenergic agonist is provided as a pharmaceutical composition comprising at least 0.25 weight percent phenylephrine. In one embodiment the long-acting alpha adrenergic agonist is provided as a pharmaceutical composition comprising 0.1 weight percent oxymetazoline and the short-acting alpha adrenergic agonist is provided as a pharmaceutical composition comprising 0.25 weight percent phenylephrine.

In one embodiment the oxymetazoline is formulated together with phenylephrine as a pharmaceutical composition comprising at least 0.1 weight percent oxymetazoline and at least 0.15 weight percent phenylephrine in an ophthalmologically acceptable carrier. In one embodiment the oxymetazoline is formulated together with the phenylephrine as a pharmaceutical composition comprising at least 0.1 weight percent oxymetazoline and at least 0.25 weight percent phenylephrine in an ophthalmologically acceptable carrier. In one embodiment the oxymetazoline is formulated together with the phenylephrine as a pharmaceutical composition comprising 0.1 weight percent oxymetazoline and 0.25 weight percent phenylephrine in an ophthalmologically acceptable carrier.

In one embodiment the administering is administering as a single drop.

In one embodiment the administering is administering at least once daily. In one embodiment the administering is administering once daily.

In one embodiment the subject does not have an allergic ocular condition calling for treatment of the eye with oxymetazoline. In one embodiment the subject does not have eyelid swelling. In one embodiment the subject has not undergone refractive eye surgery.

An aspect of the invention is a pharmaceutical composition, comprising oxymetazoline, a short-acting alpha adrenergic agonist, and a pharmaceutically acceptable carrier, formulated for topical ophthalmic use.

In one embodiment the short-acting alpha adrenergic agonist is phenylephrine.

In one embodiment the oxymetazoline is present at a concentration of at least 0.1 weight percent.

In one embodiment the phenylephrine is present at a concentration of 0.15 to 1.5 weight percent.

In one embodiment the oxymetazoline is present at a concentration of at least 0.1 weight percent and the phenylephrine is present at a concentration of at least 0.25 weight percent.

In one embodiment the oxymetazoline is present at a concentration of 0.1 weight percent and the phenylephrine is present at a concentration of 0.25 weight percent.

In one embodiment the composition further comprises an antioxidant.

In one embodiment the composition further comprises vitamin A.

In one embodiment the composition further comprises an astringent.

In one embodiment the composition further comprises a lubricant.

In one embodiment the composition further comprises a blue dye.

DETAILED DESCRIPTION OF THE INVENTION

Figure 1:
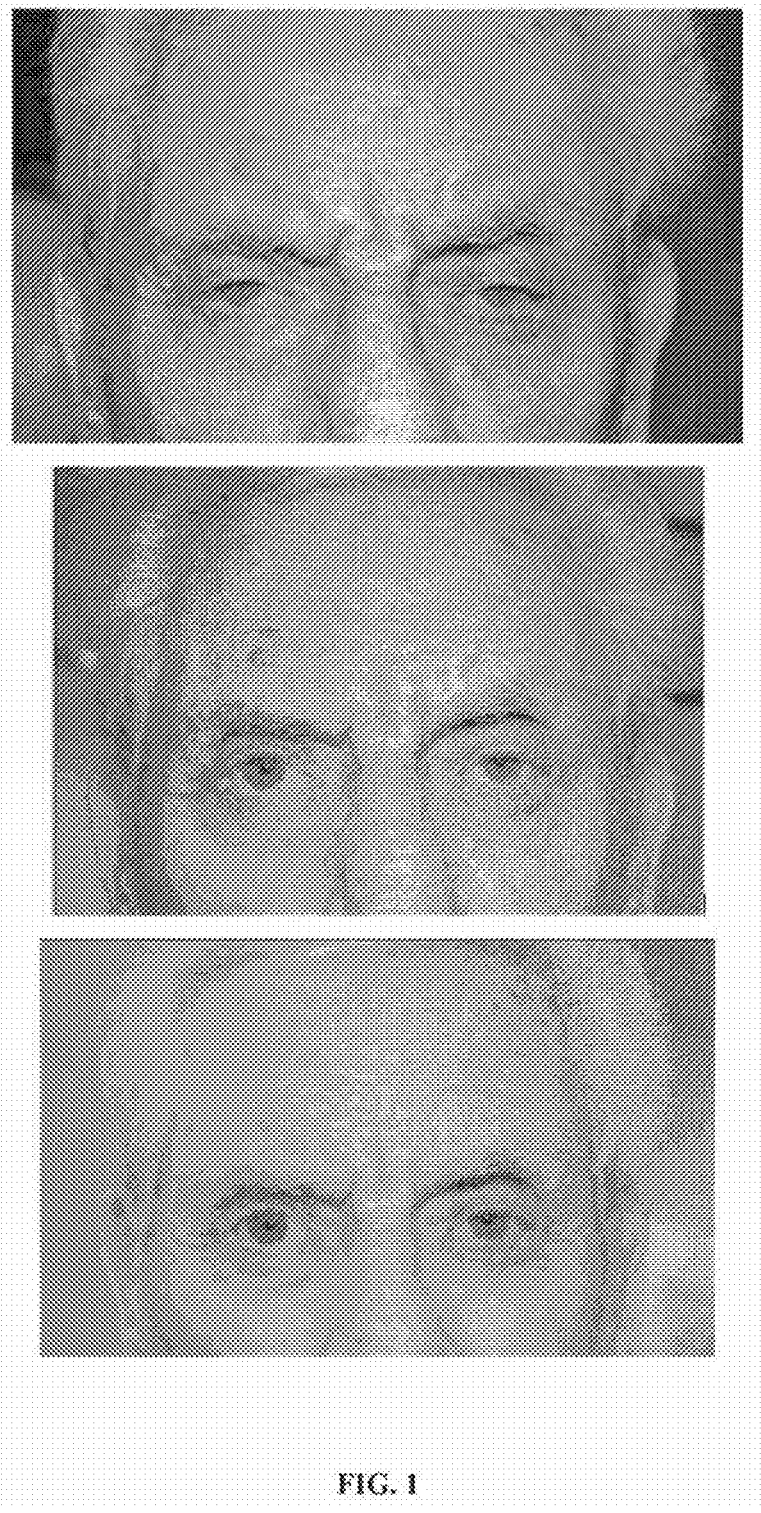
FIG. 1 is a series of three photographic images of the face of a subject before (top), 30 minutes after (middle), and 90 minutes after (bottom) topical administration of a single drop of oxymetazoline 0.1% to each eye.

The upper eyelids are normally lifted by contraction of the levator palpebrae superioris (levator) and Müller's (Mueller's) muscles. Ptosis creates a tired-looking appearance that can be cosmetically undesired; in more severe instances ptosis can interfere with vision in the affected eye(s).

In addition to fatigue and age-related weakening of the levator and Müller's muscles as underlying causes of ptosis, there are a number of other conditions recognized to cause ptosis. For example, ptosis may also be due to a myogenic, neurogenic, aponeurotic, mechanical, or traumatic cause; it usually occurs isolated, but it may be associated with various other conditions, like hereditary, immunological, or degenerative disorders, tumors, and infections.

Myogenic causes of ptosis can include diseases which may cause weakness in muscles or nerve damage, such as myasthenia gravis and chronic progressive external ophthalmoplegia. Dystrophy or dysgenesis of the levator and/or Müller's muscles are the most common causes of congenital ptosis.

Ptosis may be caused by damage to the third cranial nerve (oculomotor nerve) which controls the muscles which raise the upper eyelid. Congenital neurogenic ptosis is believed to be caused by Homer syndrome (also known as Homer's syndrome), in which a mild ptosis due to the paresis of the Müller muscle may be associated with ipsilateral miosis (pupillary constriction) and anhidrosis. Acquired Homer syndrome may result after trauma, neoplastic insult, or even vascular disease.

Acquired ptosis is commonly caused by aponeurotic ptosis. This can occur as a result of senescence, dehiscence or disinsertion of the levator aponeurosis. Moreover, chronic inflammation or intraocular surgery can lead to the same effect.

Ptosis due to trauma can ensue after an eyelid laceration with transection of the upper eyelid elevator muscles or disruption of the neural input.

Other causes of ptosis include eyelid neoplasms, neurofibromas, or the cicatrization after inflammation or surgery. Mild ptosis may occur with aging.

Compositions and methods of the invention may be particularly useful for treating ptosis in subjects with functional, or at least partially functional, levator and/or Müller's muscles and their respective aponeuroses.

The present inventor has surprisingly found, through a process of evaluating a number of agents over a range of concentrations of such agents, that certain alpha adrenergic agonists, including in particular oxymetazoline 0.1 percent, provide highly effective treatment of ptosis, lasting for several hours, following topical administration of just a single drop of such agent to an affected eye.

An aspect of the invention is a method for treating ptosis in a subject. The method includes the step of administering an effective amount of oxymetazoline to the exterior surface of an eye of a subject in need of such treatment. As used herein, "treating" means reducing, even if only temporarily, the severity of a condition or disease in a subject having such condition or disease. In one embodiment the reducing is eliminating, even if only temporarily. For example, ptosis in a subject is said to be treated in accordance with the method if the ptosis is reduced or eliminated, even if only temporarily. Also as used herein, a "subject" refers to a living mammal. In one embodiment the subject is a human. A "subject in need of such treatment" is a subject having a condition in need of treatment. For example, in the context of this aspect of the invention, a subject in need of such treatment is a subject that has ptosis of at least one eyelid.

A subject has ptosis when at least the left or the right upper eyelid is subjectively or objectively ptotic compared to historical control and/or the other eye. In one embodiment both the left and the right upper eyelid are ptotic, although not necessarily to the same degree. Historical control can be provided in the form of a photographic image, for example.

In one embodiment a subject is said to have ptosis when at least the left or the right upper eyelid is ptotic by at least one millimeter (mm) compared to historical control and/or the other eye. Such measurement involves measuring the widest separation of the upper and lower lids in the sagittal plane, typically but not necessarily across the center of the pupil, with the subject at rest, i.e., without any conscious effort on the part of the subject to widen the lids. In one embodiment the measurement is made on the eye or eyes of a living subject. In one embodiment the measurement is made or based on a photographic image of the subject's eye or eyes.

Oxymetazoline is 3-(4,5-dihydro-1H-imidazol-2-ylmethyl)-2,4-dimethyl-6-tert-butyl-phenol, CAS number 1491-59-4. It was developed from xylometazoline at E. Merck Darmstadt by Fruhstorfer in 1961 (German Patent 1,117,588).

Oxymetazoline is a well known potent alpha adrenergic agonist that finds use as a vasoconstrictor. It has been used in the form of its hydrochloride salt as the principal active agent in topical nasal decongestants such as Afrin (Schering Plough). Afrin provides 12-hour relief for sinus congestion and was first sold as a prescription medication in 1966. It has been available as an over-the-counter drug since 1975.

Oxymetazoline has also been used to treat eye redness due to minor irritation (marketed in the form of eye drops as Visine® L.R.® (Johnson & Johnson) and Ocuclear® (Schering)). Each of these eye drop formulations contains 0.025 percent oxymetazoline hydrochloride (HCl) as the active agent. Indications for Visine® L.R.® and Ocuclear® are redness due to minor eye irritation, and burning, irritation, and dryness of the eye caused by wind, sun, and other minor irritants. Ocuclear is also marketed for use in the treatment of acute allergic conjunctivitis and non-infectious conjunctivitis.

Ocular use of oxymetazoline has been described in the literature. Duzman et al. reported the characterization of ocularly administered oxymetazoline hydrochloride at 0.01 percent, 0.025 percent, and 0.05 percent for the treatment of hyperemia (redness). Duzman et al. (1983) *Arch Ophthalmol* 101:1122-6. In this report, the authors concluded that the optimal concentration of oyxmetazoline was 0.025 percent.

In a study of safety and tolerance of ophthalmic solution for possible use in treating allergic conjunctivitis, Samson et al. concluded that 0.025 percent oxymetazoline was well tolerated and subjects preferred formulation in boric acid rather than phosphate buffer. Samson et al. (1980) *Pharmatherapeutica* 2:347-52.

Additional studies have examined the use of oxymetazoline 0.004 percent to 0.025 percent for the treatment of benign red eye (Vajpayee et al. (1986) *Indian J Ophthalmol* 34:33-6) and allergic and non-infectious conjunctivitis (Fox et al. (1979) *J Int Med Res* 7:528-30; Breakly et al. (1980) *Pharmatherapeutica* 2:353-6; Duzman et al. (1986) *Ann Ophthalmol* 18:28-31; and Xuan et al. (1997) *J Ocul Pharmacol Ther* 13:363-7).

U.S. Pat. No. 6,730,691 to Galin discloses the topical application of ophthalmic solutions containing one or more alpha adrenergic blocking agents to inhibit undesirable visual anomalies, such as photophobia, glare, secondary images, and haloing, in individuals who have undergone refractive eye surgery. In one embodiment the solution includes an anti-irritant agent selected from the group consisting of naphthazoline, oxymetazoline, and tetrahydrozaline. In one embodiment such anti-irritant is disclosed to be included in a concentration of from about 0.025 percent by weight to about 0.1 percent by weight.

U.S. Pat. No. 7,022,740 to Mackles discloses lubricious ophthalmic solutions consisting essentially of an aqueous solution of a monographed polyol (e.g., polyvinyl alcohol), borate, a monographed polysorbate (e.g., monolaurate, monopalmitate, monostearate), preservative, and buffer. Mackles teaches that pharmacologically active substances soluble within such solution can be formulated together with the solution, including ophthalmic vasoconstrictors such as ephedrine HCl, naphazoline HCl, phenylephrine HCl, tetrahydrozoline HCl, and oxymetazoline HCl, the latter at 0.05 percent.

US Patent Application Publication No. 2007/0264318 by Chapin et al. discloses compositions and methods for the treatment and prevention of eyelid swelling. The compositions and methods are based on osmotically active agent and/or a vasoconstrictor and/or an astringent. In some embodiments the composition is disclosed to include a vasoconstrictor, including nephazoline, oxymetazoline, phenylephrine, or tetrahydrozine. Eyelid swelling was measured using 3D scanning technology.

An effective amount of oxymetazoline is administered to the exterior surface of an eye. As used herein, an "effective amount" is an amount that is sufficient to achieve a desired biological result. For example, an effective amount of oxymetazoline is an amount of oxymetazoline that is sufficient to treat ptosis in a subject having ptosis. The effective amount can vary depending on such factors as the disease or condition being treated, or the severity of the disease or condition. One of skill in the art may empirically determine an effective amount of a particular agent without necessitating undue experimentation.

The effective amount is administered to the eye or eyes intended for treatment. For example, if the left eyelid is ptotic, the effective amount of oxymetazoline is administered to the left eye.

Administering can be accomplished using any suitable method for topical administration of a pharmaceutical agent to the exterior surface of an eye. In one embodiment the administering involves delivering the agent in dropwise fashion to the eye. One or more drops can be administered to the eye. In one embodiment, a single drop is administered to the eye.

The exterior surface of an eye refers to any portion of the surface of an eye that is normally visible and/or accessible within the palpebral fissure, e.g., the surface of the eye that is normally exposed and/or accessible between the upper and lower eyelids. This surface can include any or all of the following structures: the cornea, the conjunctiva, and the tear sac. In one embodiment this surface is accessible without manual manipulation of the upper or lower eyelids to permit administration. In one embodiment this surface is made accessible by manually opening or widening the palpebral fissure to permit or assist in administration.

In one embodiment the method results in at least a 0.5 mm increase in the vertical separation of the upper and lower lids of the eye. The increase is the difference between the separation of the lids before treatment and separation following treatment. The vertical separation can be measured using any suitable method. In one embodiment measuring involves measuring the widest separation of the upper and lower lids in the sagittal plane, typically but not necessarily across the center of the pupil, with the subject at rest, i.e., without any conscious effort on the part of the subject to widen the lids. The measurement may be aided by asking the subject to look at a distant fixation light or point. In one embodiment the measurement is made on the eye or eyes of a living subject, for example using a fine point metric ruler. In one embodiment the measurement is made or based on a photographic image of the subject's eye or eyes, for example using a fine point metric ruler or a magnifier with a metric graticule (Edmund Scentific, Paramus, N.J.). In one embodiment the method results in at least a 1 mm increase in the vertical separation of the upper and lower lids of the eye.

The increase is the difference between the separation of the lids before treatment and the separation of the lids following treatment. For example, if the separation is 8 mm before treatment and the separation is 10 mm following treatment, the increase is 2 mm. Since there may be some time lag in reaching the maximum effect, in one embodiment the increase is the maximum increase achieved following administration of the active agent. For example, if the separation is 8 mm before treatment, 9 mm immediately after treatment, 10 mm 30 minutes after treatment, and 8 mm 16 hours after treatment, the increase is 2 mm.

Alternatively or in addition, in one embodiment the method results in at least a 5 percent increase in the vertical separation of the upper and lower lids of the eye. The vertical separation can be measured as described above, and then the percent increase calculated as: $[(D_{after}-D_{before})/D_{before}]\times 100\%$, where $D_{after}$ is the vertical separation of the lids following treatment and $D_{before}$ is the vertical separation of the lids before treatment. For example, if the separation is 8 mm before treatment and the separation is 10 mm following treatment, the percent increase is $[(10-8)/8]\times 100\%=25\%$. Since there may be some time lag in reaching the maximum effect, in one embodiment the percent increase is the maximum percent increase achieved following administration of the active agent. For example, if the separation is 8 mm before treatment, 9 mm immediately after treatment, 10 mm 30 minutes after treatment, and 8 mm 16 hours after treatment, the percent increase is $[(10-8)/8]\times 100\%=25\%$. In one embodiment the method results in at least a 10 percent increase in the vertical separation of the upper and lower lids of the eye. In one embodiment the method results in at least a 20 percent increase in the vertical separation of the upper and lower lids of the eye.

In one embodiment the oxymetazoline is formulated as a pharmaceutical composition comprising at least 0.05 weight percent oxymetazoline in an ophthalmologically acceptable carrier. In one embodiment the oxymetazoline is formulated as a pharmaceutical composition comprising at least 0.1 weight percent oxymetazoline in an ophthalmologically acceptable carrier. The invention further embraces embodiments in which a higher weight percentage of oxymetazoline is used, for example, up to and including 1.0 weight percent oxymetazoline. Accordingly, in various embodiments the oxymetazoline may be present at a concentration of 0.05, 0.1, 0.2, 0.3, 0.4, 0.5, 0.6, 0.7, 0.8, 0.9, or 1.0 weight percent, or any concentration therebetween. In one embodiment the oxymetazoline is present at a concentration of 0.1 weight percent.

As used herein, an "ophthalmologically acceptable carrier" is any pharmaceutically acceptable carrier that is suitable for topical administration to the eye.

In one embodiment the oxymetazoline is provided as a pharmaceutically acceptable salt of oxymetazoline. The term "pharmaceutically acceptable salts" is art-recognized, and refers to relatively non-toxic, inorganic and organic acid addition salts of compositions of the present invention or any components thereof, including without limitation, therapeutic agents, excipients, other materials and the like. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. Examples of suitable inorganic bases for the formation of salts include but are not limited to the hydroxides, carbonates, and bicarbonates of ammonia, sodium, lithium, potassium, calcium, magnesium, aluminum, zinc and the like. Salts may also be formed with suitable organic bases, including those that are non-toxic and strong enough to form such salts. For purposes of illustration, the class of such organic bases may include mono-, di-, and trialkylamines, such as methylamine, dimethylamine, and triethylamine; mono-, di- or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenethylamine; (trihydroxymethyl)aminoethane; and the like. See, for example, Berge et al. (1977) *J. Pharm. Sci.* 66:1-19.

In one embodiment the pharmaceutically acceptable salt of oxymetazoline is oxymetazoline hydrochloride.

When the oxymetazoline is provided as a pharmaceutically acceptable salt, in one embodiment the weight percent oxymetazoline can be based on the oxymetazoline component alone. Alternatively, when the oxymetazoline is provided as a pharmaceutically acceptable salt, the weight percent oxymetazoline can be based on the oxymetazoline salt.

In one embodiment the administering is administering as a single drop. The drop can be dispensed, for example, from a suitably constructed squeeze bottle or from a dropper. A single drop typically has a volume of about 0.1 to 0.35 milliliters (mL).

In one embodiment the administering is performed by the subject. In one embodiment the administering is performed by an individual other than the subject, e.g., by a health care provider, a parent, or a spouse.

In one embodiment the administering is administering at least once daily. The invention contemplates administration once, twice, three times, and up to four times in any given 24 hour period. For administration more than once daily, the administering can be performed over equal periods, for example every twelve hours, or unequal periods, for example at 7 a.m. and 3 p.m. (rather than 7 a.m. and 7 p.m.). In one embodiment the administering is administering once daily.

Certain subjects may be excluded from the methods of the invention. In one embodiment the subject does not have an allergic ocular condition calling for treatment of the eye with oxymetazoline. In one embodiment the subject does not have eyelid swelling. In one embodiment the subject has not undergone refractive eye surgery. In one embodiment the subject does not have an allergic ocular condition calling for treatment of the eye with oxymetazoline and the subject does not have eyelid swelling. In one embodiment the subject does not have an allergic ocular condition calling for treatment of the eye with oxymetazoline and the subject has not undergone refractive eye surgery. In one embodiment the subject does not have eyelid swelling and the subject has not undergone refractive eye surgery. In one embodiment the subject does not have an allergic ocular condition calling for treatment of the eye with oxymetazoline, does not have eyelid swelling, and has not undergone refractive eye surgery. Alternatively or in addition, in certain embodiments the subject does not have acute allergic conjunctivitis or non-infectious conjunctivitis.

An aspect of the invention is a method for treating ptosis in a subject. The method includes the step of administering an effective amount of a long-acting alpha adrenergic agonist and an effective amount of a short-acting alpha adrenergic agonist to the exterior surface of an eye of a subject in need of such treatment. As used herein, a "long-acting alpha adrenergic agonist" is an alpha adrenergic agonist with a systemic half-life in normal adult humans of greater than three hours. Long-acting alpha adrenergic agonists include, without limitation, oxymetazoline, methoxamine, naphazoline, tetrahydrozoline, xylometazoline, and apraclonidine (also known as Iopidine®). The longest acting of these agents is oxymetazoline, with a reported half-life of 5 to 6 hours. In one embodiment the long-acting alpha adrenergic agonist is a pharmaceutically acceptable salt of the long-acting alpha adrenergic agonist. In one embodiment the long-acting alpha adrenergic agonist is oxymetazoline or a pharmaceutically acceptable salt thereof, e.g., oxymetazoline hydrochloride.

As used herein, a "short-acting alpha adrenergic agonist" is an alpha adrenergic agonist with a systemic half-life in normal adult humans of less than or equal to three hours. Short-acting alpha adrenergic agonists include, without limitation, phenylephrine and brimonidine. In one embodiment the short-acting alpha adrenergic agonist is a pharmaceutically acceptable salt of the short-acting alpha adrenergic agonist. In one embodiment the short-acting alpha adrenergic agonist is phenylephrine or a pharmaceutically acceptable salt thereof, e.g., phenylephrine hydrochloride.

Phenylephrine is frequently used in pre-surgical evaluation of ptosis. Typically, to predict what result might be expected from surgical treatment of ptosis, a single drop of phenylephrine 2.5% is placed in the affected eye. There is a rapid (nearly immediate) response with lifting of the lid. However, this pharmacological response lasts for less than one hour, and it may include dilation of the pupil of the treated eye.

As disclosed in Example 8 herein, it was found that a combination of oxymetazoline, e.g., 0.1%, together with phenylephrine, e.g., 0.25%, unexpectedly acts synergistically in the treatment of ptosis. The effect of the combination is dramatically greater than not only the effect of either agent alone but also the sum of the effects of each agent alone. This synergistic effect was found to occur even with a combination including an amount of phenylephrine that induces, at most, only a minimal amount of mydriasis, i.e., clinically insignificant mydriasis.

In one embodiment the long-acting alpha adrenergic agonist is provided as a pharmaceutical composition comprising at least 0.1 weight percent oxymetazoline and the short-acting alpha adrenergic agonist is provided as a pharmaceutical composition comprising at least 0.15 weight percent phenylephrine. In one embodiment the long-acting alpha adrenergic agonist is provided as a pharmaceutical composition comprising at least 0.1 weight percent oxymetazoline and the short-acting alpha adrenergic agonist is provided as a pharmaceutical composition comprising at least 0.25 weight percent phenylephrine. In one embodiment the long-acting alpha adrenergic agonist is provided as a pharmaceutical composition comprising 0.1 weight percent oxymetazoline and the short-acting alpha adrenergic agonist is provided as a pharmaceutical composition comprising 0.25 weight percent phenylephrine.

In one embodiment oxymetazoline is formulated together with phenylephrine as a pharmaceutical composition comprising at least 0.05 weight percent oxymetazoline and at least 0.15 weight percent phenylephrine in an ophthalmologically acceptable carrier.

In one embodiment oxymetazoline is formulated together with phenylephrine as a pharmaceutical composition comprising at least 0.1 weight percent oxymetazoline and at least 0.15 percent phenylephrine in an ophthalmologically acceptable carrier. In one embodiment the oxymetazoline is formulated together with the phenylephrine as a pharmaceutical composition comprising at least 0.1 weight percent oxymetazoline and at least 0.25 weight percent phenylephrine in an ophthalmologically acceptable carrier. In one embodiment the oxymetazoline is formulated together with the phenylephrine as a pharmaceutical composition comprising 0.1 weight percent oxymetazoline and 0.25 weight percent phenylephrine in an ophthalmologically acceptable carrier.

In one embodiment the oxymetazoline is present at a concentration of at least 0.1 weight percent. In various embodiments the oxymetazoline may be present at a concentration of 0.1, 0.2, 0.3, 0.4, 0.5, 0.6, 0.7, 0.8, 0.9, or 1.0 weight percent, or any concentration therebetween. In one embodiment the oxymetazoline is present at a concentration of 0.1 weight percent.

In one embodiment the phenylephrine is present at a concentration of 0.15 to 1.5 weight percent. Accordingly, in various embodiments the phenylephrine can be present at a concentration of 0.15, 0.2, 0.3, 0.4, 0.5, 0.6, 0.7, 0.8, 0.9, 1.0, 1.1, 1.2, 1.3, 1.4, or 1.5 weight percent, or any concentration therebetween. In one embodiment the phenylephrine is present at a concentration of 0.25 weight percent.

An aspect of the invention is a pharmaceutical composition, comprising oxymetazoline, a short-acting alpha adrenergic agonist, and a pharmaceutically acceptable carrier, formulated for topical ophthalmic use. In one embodiment the oxymetazoline is provided as a pharmaceutically acceptable salt, e.g., oxymetazoline hydrochloride. In one embodiment the short-acting alpha adrenergic agonist is phenylephrine or a pharmaceutically acceptable salt thereof, e.g., phenylephrine hydrochloride.

In one embodiment the oxymetazoline is present at a concentration of at least 0.1 weight percent. In various embodiments the oxymetazoline may be present at a concentration of 0.1, 0.2, 0.3, 0.4, 0.5, 0.6, 0.7, 0.8, 0.9, or 1.0 weight percent, or any concentration therebetween. In one embodiment the oxymetazoline is present at a concentration of 0.1 weight percent.

In one embodiment the phenylephrine is present at a concentration of 0.15 to 1.5 weight percent. Accordingly, in various embodiments the phenylephrine can be present at a concentration of 0.15, 0.2, 0.3, 0.4, 0.5, 0.6, 0.7, 0.8, 0.9, 1.0, 1.1, 1.2, 1.3, 1.4, or 1.5 weight percent, or any concentration therebetween. In one embodiment the phenylephrine is present at a concentration of 0.25 weight percent.

In one embodiment the oxymetazoline is present at a concentration of at least 0.1 weight percent and the phenylephrine is present at a concentration of at least 0.25 weight percent.

In one embodiment the oxymetazoline is present at a concentration of 0.1 weight percent and the phenylephrine is present at a concentration of 0.25 weight percent.

The pharmaceutical composition optionally can include at least one additional active agent. For example, in one embodiment the pharmaceutical composition further includes an anti-oxidant. An antioxidant is a molecule capable of inhibiting the oxidation of other molecules. Oxidation is a chemical reaction that transfers electrons from a substance to an oxidizing agent. Oxidation reactions can produce free radicals. In turn, these radicals can start chain reactions that damage cells. Antioxidants terminate these chain reactions by removing free radical intermediates, and inhibit other oxidation reactions. They do this by being oxidized themselves, so antioxidants are often reducing agents such as thiols, ascorbic acid or polyphenols. Antioxidants are classified into two broad divisions, depending on whether they are soluble in water (hydrophilic) or in lipids (hydrophobic). In general, water-soluble antioxidants react with oxidants in the cell cytosol and the blood plasma, while lipid-soluble antioxidants protect cell membranes from lipid peroxidation. Water-soluble antioxidants include, without limitation, ascorbic acid (vitamin C), glutathione, lipoic acid, and uric acid. Lipid-soluble antioxidants include, without limitation, carotenes (e.g., alpha-carotene, beta-carotene), alpha-tocopherol (vitamin E), and ubiquinol (co-enzyme Q).

In one embodiment the antioxidant is N-acetylcarnosine. In one embodiment the antioxidant is sodium metabisulfite.

As a further example, in one embodiment the pharmaceutical composition further includes vitamin A (retinol). When converted to the retinal (retinaldehyde) form, vitamin A is essential for vision, and when converted to retinoic acid, is essential for skin health and bone growth. These chemical compounds are collectively known as retinoids, and possess the structural motif of all-trans retinol as a common feature in their structure. Topical vitamin A, for example in the form of eye drops containing retinyl palmitate 0.05 percent, has been reported to be effective treatment for dry eye (also known as keratoconjunctivitis sicca, xerophthalmia, and dry eye syndrome). Kim et al. (2009) *Am J Ophthalmol* 147: 206-13. Vitamin A has also been formulated at a strength of 50,000 units/mL for ophthalmic use.

In one embodiment the pharmaceutical composition further includes an astringent. Astringents include, but are not limited to, witch hazel, zinc sulfate, silver sulfate, plant tannins, oak bark extract, bird cherry extract, and natural flavinoids. In one embodiment the astringent is witch hazel, which is an astringent produced from the leaves and bark of the North American Witch Hazel shrub (*Hamamelis virginiana*), which grows naturally from Nova Scotia west to Ontario, Canada, and south to Florida and Texas in the United States. Witch hazel is readily available from a number of commercial suppliers, including Dickinson's and Henry Thayer.

The pharmaceutical composition optionally can include at least one additional inert or non-active agent. In one embodiment the pharmaceutical composition further includes a lubricant. Ocular lubricants are solutions, gels, or ointments formulated to moisturize the eyes. Included among ocular lubricants are artificial tears, such as are available from any of a variety of commercial suppliers. In certain embodiments, such lubricants typically may include an aqueous solution of a polyalcohol (polyol) such as polyvinyl alcohol, borate, and a buffer. In certain embodiment, ocular lubricants may include white petrolatum and mineral oil.

In one embodiment the pharmaceutical composition further includes a blue dye, e.g., methylene blue. The blue dye confers a lightening or whitening effect on the sclera, thereby making "tired eyes" appear less tired.

The phrase "pharmaceutically acceptable carrier" is art-recognized, and refers to, for example, pharmaceutically acceptable materials, compositions or vehicles, such as a liquid or solid filler, diluent, excipient, solvent or encapsulating material, involved in carrying or transporting any supplement or composition, or component thereof, from one organ, or portion of the body, to another organ, or portion of the body. Each carrier must be "acceptable" in the sense of being compatible with the other ingredients of the supplement and not injurious to the patient. In certain embodiments, a pharmaceutically acceptable carrier is non-pyrogenic. Some examples of materials which may serve as pharmaceutically acceptable carriers include: pyrogen-free water; aqueous solutions, suspensions, and ointments; isotonic saline; Ringer's solution; phosphate buffer solutions; borate solutions; sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, sunflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; ethyl alcohol; and other non-toxic compatible substances employed in pharmaceutical formulations.

Featured are novel topical pharmaceutical compositions comprising an effective amount of one or more active agents in a pharmaceutically acceptable carrier for the treatment and prevention of ptosis and/or "tired eyes". Such formulations provide a comfortable formulation when instilled in the eye. The one or more active agents may include, but are not limited to, alpha adrenergic agonists and, optionally, one or more astringent agents, antioxidants, vitamin A, and any combination thereof.

In one embodiment, the pharmaceutical compositions of the invention comprise one or more active ingredients formulated in an aqueous solution. Alternatively or in addition, the pharmaceutical compositions may be formulated for topical administration as solutions, suspensions, oils, viscous or semi-viscous gels, emulsions, liposomes, lotions, ointments, creams, gels, salves, powders, and sustained or slow release, or other types of solid or semi-solid compositions, including formulations described in U.S. Pat. No. 6,806,364. The compositions may also be topically administered in a sprayable form.

In one embodiment the pharmaceutical compositions includes a tear substitute. A variety of tear substitutes are known in the art, including but not limited to: polyols such as, glycerol, glycerin, polyethylene glycol 300, polyethylene glycol 400, polysorbate 80, propylene glycol, and ethylene glycol, polyvinyl alcohol, povidone, and polyvinylpyrrolidone; cellulose derivatives such hydroxypropyl methylcellulose (also known as hypromellose), carboxy methylcellulose sodium, hydroxypropyl cellulose, hydroxyethyl cellulose, and methylcellulose; dextrans such as dextran 70; water soluble proteins such as gelatin; carbomers such as carbomer 934P, carbomer 941, carbomer 940 and carbomer 974P; and gums such as HP-guar. Many such tear substitutes are commercially available, which include, but are not limited to cellulose esters such as Bion Tears®, Celluvisc®, Genteal®, OccuCoat®, Refresh®, Teargen II®, Tears Naturale®, Tears Naturale 118®, Tears Naturale Free®, and TheraTears®; and polyvinyl alcohols such as Akwa Tears®, HypoTears®, Moisture Eyes®, Murine Lubricating®, and Visine Tears®. In other embodiments, the tear substitute is that which is described in U.S. Pat. No. 6,806,364, which is expressly incorporated by reference herein in its entirety. The formulation described in U.S. Pat. No. 6,806,364 contains 0.2 to 2.5 (e.g., 0.5 to 0.8) percent by weight of hydroxypropyl methylcellulose, 0.045 to 0.065 (e.g., 0.05 to 0.06) percent by weight a calcium salt, and 0.14 to 1.4 (e.g., 0.3 to 1.2) percent by weight a phosphate salt. The formulation described in U.S. Pat. No. 6,806,364 has a viscosity of 20 to 150 (e.g., 50 to 90) centipoise and is buffered to a pH 5.5 to 8.5 (e.g., 6 to 8) with a phosphate salt or other suitable salts. It may further contain one or more of the following ingredients: 0.5 to 1.0 percent by weight glycerol, 0.5 to 1.0 percent by weight propyleneglycerol, 0.005 to 0.05 percent by weight glycine, 0.006 to 0.08 percent by weight sodium borate, 0.025 to 0.10 percent by weight magnesium chloride, and 0.001 to 0.01 percent by weight zinc chloride.

Tear substitutes may also be comprised of paraffins, such as the commercially available Lacri-Lube® ointments. Other commercially available ointments that are used as tear substitutes include Lubrifresh PM®, Moisture Eyes PM®, and Refresh PM®.

The pharmaceutical compositions may be formulated for topical administration as solutions, suspensions, oils, viscous or semi-viscous gels, emulsions, liposomes, lotions, ointments, creams, gels, salves, powders, and sustained or slow release, or other types of solid or semi-solid compositions, including formulations described in U.S. Pat. No. 6,806,364. The composition may also be topically administered in a sprayable form.

Any of a variety of carriers may be used in the formulations of the present invention, including water, mixtures of water and water-miscible solvents, such as, but not limited to, C1- to C7-alkanols, vegetable oils or mineral oils comprising from 0.5 to 5% non-toxic water-soluble polymers, natural products, such as gelatin, alginates, pectins, tragacanth, karaya gum, xanthan gum, carrageenin, agar and acacia, starch derivatives, such as starch acetate and hydroxypropyl starch, and also other synthetic products, such as polyvinyl alcohol, polyvinylpyrrolidone, polyvinyl methyl ether, polyethylene oxide, preferably cross-linked polyacrylic acid, such as neutral Carbopol, or mixtures of those polymers. The concentration of the carrier is, typically, from 1 to 100,000 times the concentration of the active ingredient.

Additional ingredients that may be included in the formulation include tonicity enhancers, preservatives, solubilizers, non-toxic excipients, demulcents, sequestering agents, pH adjusting agents, co-solvents and viscosity building agents.

For the adjustment of the pH, preferably to a physiological pH, buffers may be especially useful. The pH of the present solutions should be maintained within the range of 4.0 to 8.0, more preferably about 4.0 to 6.0, more preferably about 6.5 to 7.8. Suitable buffers may be added, such as, but not limited to, boric acid, sodium borate, potassium citrate, citric acid, sodium bicarbonate, TRIS, and various mixed phosphate buffers (including combinations of $Na_2HPO_4$, $NaH_2PO_4$, and $KH_2PO_4$) and mixtures thereof. Generally, buffers will be used in amounts ranging from about 0.05 to 2.5 percent by weight, and preferably, from 0.1 to 1.5 percent.

Tonicity is adjusted, if needed, typically by tonicity enhancing agents. Such agents may, for example, be of ionic and/or non-ionic type. Examples of ionic tonicity enhancers include, but are not limited to, alkali metal or alkaline earth metal halides, such as, for example, $CaCl_2$), KBr, KCl, LiCl, NaI, NaBr, NaCl, $Na_2SO_4$, or boric acid. Non-ionic tonicity enhancing agents are, for example, urea, glycerol, sorbitol, mannitol, propylene glycol, or dextrose. These agents may also serve as the active agents in certain embodiments. The aqueous solutions of the present invention are typically adjusted with tonicity agents to approximate the osmotic pressure of normal lachrymal fluids which is equivalent to a 0.9% solution of sodium chloride or a 2.5% solution of glycerol. An osmolality of about 225 to 400 mOsm/kg is preferred, more preferably 280 to 320 mOsm.

In certain embodiments, the topical formulations additionally comprise a preservative. A preservative may typically be selected from a quaternary ammonium compound such as benzalkonium chloride (N-benzyl-N—(C8-C18 alkyl)-N,N-dimethylammonium chloride), benzoxonium chloride, or the like. Examples of preservatives different from quaternary ammonium salts are alkyl-mercury salts of thiosalicylic acid, such as, for example, thimerosal (also known as thiomersal), phenylmercuric nitrate, phenylmercuric acetate or phenylmercuric borate, sodium perborate, sodium chlorite, parabens, such as, for example, methylparaben or propylparaben, alcohols, such as, for example, chlorobutanol, benzyl alcohol or phenyl ethanol, guanidine derivatives, such as, for example, chlorhexidine or polyhexamethylene biguanide, sodium perborate, Germal® II or sorbic acid. Preferred preservatives are quaternary ammonium compounds, in particular benzalkonium chloride or its derivative such as Polyquad (see U.S. Pat. No. 4,407,791), alkyl-mercury salts and parabens. Where appropriate, a sufficient amount of preservative is added to the ophthalmic composition to ensure protection against secondary contaminations during use caused by bacteria and fungi.

In another embodiment, the topical formulations of this invention do not include a preservative. Such formulations would be useful for patients who wear contact lenses, or those who use several topical ophthalmic drops and/or those with an already compromised ocular surface (e.g. dry eye) wherein limiting exposure to a preservative may be desirable.

The topical formulation may additionally include a solubilizer, in particular if the active or the inactive ingredients tend to form a suspension or an emulsion. A solubilizer suitable for an above-concerned composition is for example selected from the group consisting of tyloxapol, fatty acid glycerol polyethylene glycol esters, fatty acid polyethylene glycol esters, polyethylene glycols, glycerol ethers, a cyclodextrin (for example alpha-, beta- or gamma-cyclodextrin, e.g. alkylated, hydroxyalkylated, carboxyalkylated or alkyloxycarbonyl-alkylated derivatives, or mono- or diglycosyl-alpha-, beta- or gamma-cyclodextrin, mono- or dimaltosyl-alpha-, beta- or gamma-cyclodextrin, or panosyl-cyclodextrin), polysorbate 20, polysorbate 80, or mixtures of those compounds. In one embodiment the solubilizer is a reaction product of castor oil and ethylene oxide, for example the commercial products Cremophor EL® or Cremophor RH40®. Reaction products of castor oil and ethylene oxide have proved to be particularly good solubilizers that are tolerated extremely well by the eye. Another preferred solubilizer is selected from tyloxapol and from a cyclodextrin. The concentration used depends especially on the concentration of the active ingredient. The amount added is typically sufficient to solubilize the active ingredient. For example, in one embodiment the concentration of the solubilizer is from 0.1 to 5000 times the concentration of the active ingredient.

The formulations may comprise further non-toxic excipients, such as, for example, emulsifiers, wetting agents or fillers, such as, for example, the polyethylene glycols designated 200, 300, 400 and 600, or Carbowax designated 1000, 1500, 4000, 6000 and 10000. The amount and type of excipient added is in accordance with the particular requirements and is generally in the range of from approximately 0.0001 to approximately 90% by weight.

Other compounds may also be added to the formulations of the present invention to increase the viscosity of the carrier. Examples of viscosity enhancing agents include, but are not limited to: polysaccharides, such as hyaluronic acid and its salts, chondroitin sulfate and its salts, dextrans, various polymers of the cellulose family; vinyl polymers; and acrylic acid polymers.

The dosage of any compound of the present invention will vary depending on the symptoms, age, and other physical characteristics of the patient, the nature and severity of the disorder to be treated or prevented, the degree of comfort desired, the route of administration, and the form of the medicament. Any of the subject formulations may be administered in a single dose or in divided doses. Dosages for the formulations of the present invention may be readily determined by techniques known to those of skill in the art or as taught herein.

An effective dose or amount, and any possible effects on the timing of administration of the formulation, may need to be identified for any particular formulation of the present invention. This may be accomplished by routine experiment as described herein. The effectiveness of any formulation and method of treatment or prevention may be assessed by administering the formulation and assessing the effect of the administration by measuring one or more indices associated with the efficacy of the agent and with the degree of comfort to the patient, as described herein, and comparing the post-treatment values of these indices to the values of the same indices prior to treatment or by comparing the post-treatment values of these indices to the values of the same indices using a different formulation.

The precise time of administration and amount of any particular formulation that will yield the most effective treatment in a given patient will depend upon the activity, pharmacokinetics, and bioavailability of a particular compound, physiological condition of the patient (including age, sex, disease type and stage, general physical condition, responsiveness to a given dosage and type of medication), and the like. The guidelines presented herein may be used to optimize the treatment, e.g., determining the optimum time and/or amount of administration, which will require no more than routine experimentation consisting of monitoring the subject and adjusting the dosage and/or timing.

The combined use of several agents formulated into the compositions of the present invention may reduce the required dosage for any individual component because the onset and duration of effect of the different components may be complimentary or even synergistic. In such combined therapy, the different agents may be delivered together or separately, and simultaneously or at different times within the day.

The formulations of the present invention may be packaged as either a single-dose product or a multi-dose product. The single-dose product is sterile prior to opening of the package and all of the composition in the package is intended to be consumed in a single application to one or both eyes of a patient. The use of an antimicrobial preservative to maintain the sterility of the composition after the package is opened is optional.

Multi-dose products are also sterile prior to opening of the package. However, because the container for the composition may be opened many times before all of the composition in the container is consumed, the multi-dose products typically have sufficient antimicrobial activity to ensure that the compositions will not become contaminated by microbes as a result of the repeated opening and handling of the container. The level of antimicrobial activity required for this purpose is well known to those skilled in the art, and is specified in official publications, such as the United States Pharmacopoeia ("USP"), other publications by the Food and Drug Administration, and corresponding publications in other countries. Detailed descriptions of the specifications for preservation of ophthalmic pharmaceutical products against microbial contamination and the procedures for evaluating the preservative efficacy of specific formulations are provided in those publications. In the United States, preservative efficacy standards are generally referred to as the "USP PET" requirements. (The acronym "PET" stands for "preservative efficacy testing".)

The use of a single-dose packaging arrangement eliminates the need for an antimicrobial preservative in the compositions, which is a significant advantage from a medical perspective, because conventional antimicrobial agents utilized to preserve ophthalmic compositions (e.g., benzalkonium chloride) may cause ocular irritation, particularly in patients suffering from dry eye conditions or pre-existing ocular irritation. However, the single-dose packaging arrangements currently available, such as small volume plastic vials prepared by means of a process known as "form, fill and seal", have several disadvantages for manufacturers and consumers. The principal disadvantages of the single-dose packaging systems are the much larger quantities of packaging materials required, which is both wasteful and costly, and the inconvenience for the consumer. Also, there is a risk that consumers will not discard the single-dose containers following application of one or two drops to the eyes, as they are instructed to do, but instead will save the opened container and any composition remaining therein for later use. This improper use of single-dose products creates a risk of microbial contamination of the single-dose product and an associated risk of ocular infection if a contaminated composition is applied to the eyes.

While the formulations of this invention are preferably formulated as "ready for use" aqueous solutions, alternative formulations are contemplated within the scope of this invention. Thus, for example, the active ingredients, surfactants, salts, chelating agents, or other components of the ophthalmic solution, or mixtures thereof, can be lyophilized or otherwise provided as a dried powder or tablet ready for dissolution (e.g., in deionized, or distilled) water.

In still another embodiment, this invention provides kits for the packaging and/or storage and/or use of the formulations described herein, as well as kits for the practice of the methods described herein. Thus, for example, kits may comprise one or more containers containing one or more ophthalmic preparations, tablets, or capsules of this invention. The kits can be designed to facilitate one or more aspects of shipping, use, and storage.

The kits may optionally include instructional materials containing directions (i.e., protocols) disclosing means of use of the formulations provided therein. While the instructional materials typically comprise written or printed materials, they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The invention, having been generally described, may be more readily understood by reference to the following examples, which are included merely for purposes of illustration of certain aspects and embodiments of the present invention, and are not intended to limit the invention in any way.

Example 1

Non-Blinded, Uncontrolled Study with 0.1% Oxymetazoline in Subjects with Unilateral Ptosis In this example, a single drop of 0.1% oxymetazoline solution was placed in the affected eye of each of five adult human subjects with unilateral ptosis. Palpebral fissure was measured at baseline (pre-treatment), then at 30 minutes and at 4 hours following treatment. Measurements were taken with a fine point metric ruler, measuring (in mm) the central diameter of the palpebral fissure (i.e., sagitally across the center of the pupil). Results are shown in Table 1. "OD" refers to right eye; "OS" refers to left eye. "Rx" refers to which eye was treated. "% Δ (4 hr)" is the percent change 4 hours following treatment. All measurements are reported in mm. As shown in Table 1, 0.1% oxymetazoline vertically widened the palpebral fissure in 5/5 (100%) of subjects, and this effect lasted at least 4 hours. The mean increase from baseline, 4 hours following treatment, was 2 mm or 31.4%.

TABLE 1

Subjects with Unilateral Ptosis

| | | | Baseline | | 30 min | | 4 hr | | % Δ (4 hr) | |
|---|---|---|---|---|---|---|---|---|---|---|
| Patient | Age | Rx | OD | OS | OD | OS | OD | OS | OD | OS |
| 1 | 70 | OS | 8 | 6 | 7 | 9 | 8 | 9 | | 50 |
| 2 | 37 | OS | 9 | 8 | 9 | 9 | 9 | 9 | | 11 |
| 3 | 45 | OD | 5 | 6 | 7 | 6 | 8 | 6 | 60 | |
| 4 | 31 | OD | 9 | 10 | 10 | 8 | 10 | 9 | 11 | |
| 5 | 39 | OD | 8 | 9 | 9 | 7 | 10 | 8 | 25 | |

Example 2

Double-Blind, Randomized, Controlled Study with 0.1% Oxymetazoline v. Vehicle Alone in Normal Subjects In this example, a single drop of 0.1% oxymetazoline solution was randomly assigned to be placed in one eye of each of five normal adult human subjects; a single drop of vehicle alone (negative control) was placed in the other eye of each subject. Palpebral fissure was measured at baseline (pre-treatment), then at 1 hour and at 4 hours following treatment. Measurements were taken with a fine point metric ruler, measuring (in mm) the central diameter of the palpebral fissure (i.e., sagitally across the center of the pupil). Results are shown in Table 2. "OD" refers to right eye; "OS" refers to left eye. "Rx" refers to treatment. "Oxy" refers to oxymetazoline; "V" refers to vehicle. "% Δ (4 hr)" is the percent change 4 hours following treatment. All measurements are reported in mm. As shown in Table 2, 0.1% oxymetazoline vertically widened the palpebral fissure in 5/5 (100%) of subjects, and this effect lasted at least 4 hours. The mean increase from baseline, 4 hours following treatment, was 1.4 mm or 15.4%.

TABLE 2

Normal Subjects

| | | Rx | | Baseline | | 1 hr | | 4 hr | | % Δ (4 hr) | |
|---|---|---|---|---|---|---|---|---|---|---|---|
| Patient | Age | OD | OS | OD | OS | OD | OS | OD | OS | OD | OS |
| 7 | 60 | V | Oxy | 9 | 9 | 9 | 10 | 8 | 10 | | 11 |
| 8 | 29 | V | Oxy | 9 | 9 | 8 | 10 | 8 | 10 | | 11 |
| 9 | 35 | V | Oxy | 10 | 10 | 10 | 12 | 10 | 12 | | 20 |
| 6 | 39 | Oxy | V | 8 | 9 | 9 | 7 | 10 | 8 | 25 | |
| 10 | 29 | Oxy | V | 10 | 10 | 10 | 9 | 11 | 10 | 10 | |

Example 3

Double-Blind, Randomized, Controlled Study with 0.1% Oxymetazoline v. Visine® L.R.® in Normal Subjects In this example, a single drop of 0.1% oxymetazoline solution was randomly assigned to be placed in one eye of each of ten normal adult human subjects; a single drop of 0.025% oxymetazoline (Visine® L.R.®, positive control) was placed in the other eye of each subject. Palpebral fissure was measured at baseline (pre-treatment), then at 30 minutes and at 3 hours following treatment. Measurements were taken with a fine point metric ruler, measuring (in mm) the central diameter of the palpebral fissure (i.e., sagitally across the center of the pupil). Results are shown in Table 3. "OD" refers to right eye; "OS" refers to left eye. "Rx" refers to treatment. "Oxy" refers to 0.1% oxymetazoline; "Vis" refers to Visine® L.R. (0.025% oxymetazoline). "% Δ (3 hr)" is the percent change 3 hours following treatment. All measurements are reported in mm. As shown in Table 3, 0.1% oxymetazoline vertically widened the palpebral fissure to a greater extent than did 0.025% oxymetazoline (Visine® L.R.®) in 9/10 (90%) of subjects. The mean change from baseline, 3 hours following treatment with 0.1% oxymetazoline, was 1 mm or 11.2%. The mean change from baseline, 3 hours following treatment with 0.025% oxymetazoline, was −0.1 mm or −0.8%.

The negative mean change for subjects receiving 0.025% oxymetazoline reflects Hering's Law of equal innervation, whereby the upper eyelid with a weaker stimulus (e.g., 0.025% oxymetazoline) will tend to drop, while the eyelid with the stronger stimulus (e.g., 0.1% oxymetazoline) will elevate.

TABLE 3

Normal Subjects

| | | Rx | | Baseline | | 30 min | | 3 hr | | % Δ (3 hr) | |
|---|---|---|---|---|---|---|---|---|---|---|---|
| Patient | Age | OD | OS | OD | OS | OD | OS | OD | OS | Oxy | Vis |
| 12 | 23 | Vis | Oxy | 10 | 10 | 10 | 11 | 10 | 11 | 10 | 0 |
| 14 | 35 | Vis | Oxy | 9 | 10 | 12 | 11 | 10 | 10 | 0 | 11 |

TABLE 3-continued

Normal Subjects

| | | Rx | | Baseline | | 30 min | | 3 hr | | % Δ (3 hr) | |
|---|---|---|---|---|---|---|---|---|---|---|---|
| Patient | Age | OD | OS | OD | OS | OD | OS | OD | OS | Oxy | Vis |
| 15 | 60 | Vis | Oxy | 9 | 9 | 8 | 11 | 9 | 10 | 11 | 0 |
| 18 | 29 | Vis | Oxy | 9 | 9 | 9 | 10 | 9 | 10 | 11 | 0 |
| 20 | 39 | Vis | Oxy | 9 | 9 | 9 | 10 | 9 | 10 | 11 | 0 |
| 11 | 26 | Oxy | Vis | 9 | 10 | 9 | 10 | 10 | 9 | 11 | −10 |
| 13 | 29 | Oxy | Vis | 9 | 9 | 11 | 10 | 11 | 10 | 22 | 11 |
| 16 | 28 | Oxy | Vis | 7 | 9 | 9 | 8 | 8 | 8 | 14 | −11 |
| 17 | 58 | Oxy | Vis | 9 | 9 | 11 | 10 | 11 | 10 | 22 | 11 |
| 19 | 24 | Oxy | Vis | 10 | 10 | 10 | 8 | 10 | 8 | 0 | −20 |

Example 4

Single Drop Administration of 0.1% Oxymetazoline v. Repeated Administration of 0.025% Oxymetazoline (Visine® L.R.®)

A subject with pronounced ptosis of both eyelids was treated with a single drop of Visine® L.R.® to each eye, followed 15 minutes later by administration of a second single drop of Visine® L.R.® to each eye. Photographs of the subject's face were taken before the first and second treatments and again 30 minutes after the first dose. There was little or no response to the first or second treatments. Some days later, the same subject was treated with a single drop of oxymetazoline 0.1% to each eye. Photographs of the subject's face were taken before treatment and then minutes following treatment. Results are shown in FIG. 1. The top panel shows the subject prior to receiving the single drop of 0.1% oxymetazoline to each eye. The middle panel shows the subject 30 minutes after receiving the single drop of 0.1% oxymetazoline to each eye. The bottom panel shows the subject 90 minutes after receiving the single drop of 0.1% oxymetazoline to each eye. This example shows that treatment with a single drop of 0.1% oxymetazoline is dramatically more effective than repeated administration of 0.025% oxymetazoline.

Example 5

Single Drop Administration of 0.1% Oxymetazoline

Figure 2:
FIG. 2 is a series of three photographic images of the face of a subject before (top), and 25 minutes (middle) and three and one-half hours (bottom) following topical administration of a single drop of oxymetazoline 0.1% to the subject's left eye.
Figure 2:
Figure 2:
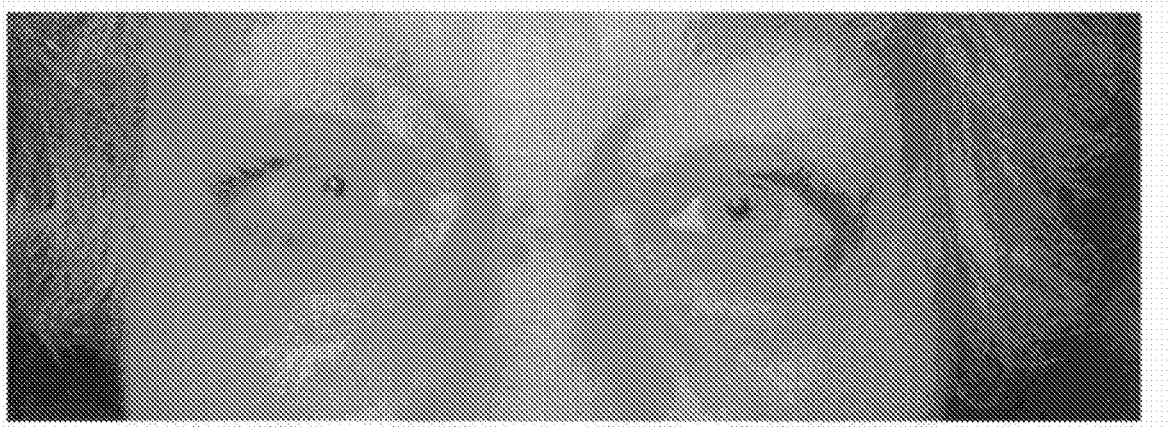

A subject with moderate ptosis of the left eyelid was treated with a single drop of 0.1% oxymetazoline administered topically to the left eye. Photographs of her face were taken before and then 25 minutes and 3.5 hours after treatment. Results are shown in FIG. 2. As shown in the figure, the ptosis was dramatically improved, in fact essentially resolved during the period of observation, following treatment with the single drop of 0.1% oxymetazoline. Although not shown in FIG. 2, the effect lasted at least six hours.

Example 6

Combination of Oxymetazoline and Phenylephrine

A normal adult human subject was treated with a single drop of a combination formulation of 0.1% oxymetazoline and 1.25% phenylephrine to both eyes. Photographs of the subject's face were taken before treatment and then 30 minutes and 45 minutes following treatment. Both eyes were wider, and both pupils were mildly dilated, at 30 and 45 minutes after treatment.

A second normal adult human subject was treated with a single drop of 0.1% oxymetazoline to the right eye, and a single drop of a combination formulation of 0.1% oxymetazoline and 1.25% phenylephrine to the left eye. Photographs of the subject's face were taken before treatment and then 30 minutes and 45 minutes following treatment. Both eyes were wider, with the left eye visibly wider than the right eye, 30 and 45 minutes after treatment. The pupil of the left eye was mildly dilated following treatment as compared to before treatment and as compared to the pupil of the right following treatment.

Example 7

Absence of Effect on Pupil Size with 0.1% Oxymetazoline in Normal Subjects

In this example, a single drop of 0.1% oxymetazoline solution was placed in each eye of six normal subjects. Pupils were measured at baseline and 30 minutes following administration of oxymetazoline. Results are shown in Table 4. "OD" refers to right eye; "OS" refers to left eye. "Baseline" refers to before treatment. "30 min" refers to 30 minutes following administration of 0.1% oxymetazoline). All measurements are reported in mm.

TABLE 4

Effect of Oxymetazoline 0.1% on Pupil Size (mm) in Normal Subjects

| | | | Baseline | | 30 min | | Δ | |
|---|---|---|---|---|---|---|---|---|
| Patient | Age | Eye Color | OD | OS | OD | OS | OD | OS |
| 21 | 60 | Blue | 3 | 3 | 3 | 3 | 0 | 0 |
| 22 | 35 | Dk Brown | 4 | 4 | 4 | 4 | 0 | 0 |
| 23 | 24 | Dk Brown | 5 | 5 | 5 | 5 | 0 | 0 |
| 24 | 39 | Lt Brown | 5 | 5 | 5 | 5 | 0 | 0 |
| 25 | 31 | Lt Brown | 6 | 6 | 6 | 6 | 0 | 0 |
| 26 | 84 | Blue | 4 | 4 | 4 | 4 | 0 | 0 |

As is evident from the results shown in Table 4, 0.1% oxymetazoline had no effect on pupil size in any of the normal subjects studied in this example. This lack of effect on pupil size is in stark contrast to the pupillary dilation (mydriasis) commonly obtained with other alpha agonists topically administered to the eye.

Example 8

Synergistic Lid Elevation Effect with 0.1% Oxymetazoline/0.25% Phenylephrine Combination In this example a study was performed to assess whether the combination of oxymetazoline 0.1% and phenylephrine 0.25% would be more potent at widening the palpebral fissure than either of the components on their own. A total of 7 patients were studied, 3 with ptosis and 4 without ptosis. On a first day, each patient received a single combination drop in one eye and oxymetazoline 0.1% alone in the other. On a second day, each subject received the same single combination drop in one eye and phenylephrine 0.25% in the other eye. This method allowed a "head to head" comparison between the two eyes. On each occasion, separation of the lids (mm) and pupil diameters (mm) were measured prior to treatment and then 30 minutes after treatment (optimal time for phenylephrine effect). Measurements were made as in the previous examples. Results are shown in Table 5 and Table 6.

TABLE 5

Combination of Oxymetazoline 0.1% and Phenylephrine 0.25% vs. Oxymetazoline 0.1% Alone
Combination vs. Oxymetazoline 0.1% Alone

| Patient | ptosis | Rx OD | Rx OS | Lids baseline OD | Lids baseline OS | Lids 30 min OD | Lids 30 min OS | Pupils baseline OD | Pupils baseline OS | Pupils 30 min OD | Pupils 30 min OS |
|---|---|---|---|---|---|---|---|---|---|---|---|
| 27 | Yes | oxy | combo | 10 | 9 | 11 | 11 | 4 | 4 | 4 | 5 |
| 28 | Yes | combo | oxy | 8 | 9 | 10 | 10 | 4 | 4 | 4 | 4 |
| 29 | Yes | combo | oxy | 8 | 9 | 9 | 8 | 4 | 4 | 4 | 4 |
| 30 | No | combo | oxy | 10 | 10 | 12 | 11 | 5 | 5 | 5 | 5 |
| 31 | No | combo | oxy | 10 | 10 | 12 | 11 | 4 | 4 | 5 | 4 |
| 32 | No | combo | oxy | 9 | 9 | 11 | 10 | 3 | 3 | 3 | 3 |
| 33 | No | combo | oxy | 10 | 10 | 12 | 11 | 5 | 5 | 6 | 5 |

TABLE 6

Combination of Oxymetazoline 0.1% and Phenylephrine 0.25% vs. Phenylephrinc 0.25% Alone
Combination vs. Phonylephrine 0.25% Alone

| Patient | ptosis | Rx OD | Rx OS | Lids baseline OD | Lids baseline OS | Lids 30 min OD | Lids 30 min OS | Pupils baseline OD | Pupils baseline OS | Pupils 30 min OD | Pupils 30 min OS |
|---|---|---|---|---|---|---|---|---|---|---|---|
| 27 | Yes | phe | combo | 9 | 8 | 10 | 10 | 5 | 5 | 6 | 6 |
| 28 | Yes | combo | phe | 8 | 9 | 10 | 9 | 4 | 4 | 4 | 4 |
| 29 | Yes | combo | phe | 7 | 8 | 9 | 8 | 5 | 5 | 5 | 5 |
| 30 | No | combo | phe | 10 | 10 | 12 | 10 | 5 | 5 | 6 | 6 |
| 31 | No | combo | phe | 10 | 10 | 12 | 10 | 3 | 3 | 4 | 4 |
| 32 | No | combo | phe | 10 | 10 | 11 | 10 | 3 | 3 | 4 | 4 |
| 33 | No | combo | phe | 10 | 10 | 12 | 10 | 5 | 5 | 5 | 5 |

Results shown in Tables 5 and 6 can be summarized as follows. For all patients, the combination of oxymetazoline 0.1% and phenylephrine 0.25% ("combo") caused a 20% increase in lid aperture; in contrast, oxymetazoline 0.1% alone ("oxy") caused a 7% increase in lid aperture and phenylephrine 0.25% alone ("phe") caused only a 2% increase in lid aperture. For patients with ptosis, the combination of oxymetazoline 0.1% and phenylephrine 0.25% caused a 21% increase in lid aperture, whereas oxymetazoline 0.1% alone caused a 3% increase in lid aperture and phenylephrine 0.25% alone caused a 4% increase in lid aperture. For patients without ptosis, the combination of oxymetazoline 0.1% and phenylephrine 0.25% caused a 19% increase in lid aperture, whereas oxymetazoline 0.1% alone caused a 10% increase in lid aperture and phenylephrine 0.25% alone ("phe") caused no change (0% increase) in lid aperture.

It should be pointed out that the lid aperture widening with oxymetazoline alone in Table 5 is less compared to the other examples because of Hering's law. (A more potent combination in the opposite eye will diminish the effect in the eye treated with oxymetazoline alone.)

In addition, for all patients, mean pupil change with the combination of oxymetazoline 0.1% and phenylephrine 0.25% was 0.4 mm; in contrast, mean pupil change for oxymetazoline 0.1% alone was 0 mm and for phenylephrine 0.25% alone was 0.4 mm.

As can be seen from Tables 5 and 6, the combination drop exerted a more profound effect on lid separation than either of the two components alone. In fact, the combination drop exerted a more profound effect on lid separation than the sum of the effects of the two components alone, i.e., the combination of oxymetazoline 0.1% and phenylephrine 0.25% exerted a synergistic effect.

Consistent with Example 7, treatment with oxymetazoline alone caused no pupillary dilation (mydriasis). In contrast to treatment with oxymetazoline alone, there was some pupil dilation with the oxymetazoline/phenylephrine combination. However, the studied combination, with 0.25% phenylephrine, did not cause a clinically significant mydriasis.

Example 9

Improvement in Visual Fields with 0.1% Oxymetazoline in Subjects with Ptosis

Visual field refers to the area projected onto the retina of and perceived by an eye. In a visual field test a patient places his or her face in a little "dome" and stares at a central light. Smaller target lights illuminate in the peripheral parts of the dome, and the patient clicks a button every time he or she sees a target light. A computer records the number (and location) of spots seen versus not seen. In addition to providing a map of each eye's visual field, the test can be summarized in terms of the percent of target lights seen by each eye. For example, in a visual field test with 36 target lights, a score of 25% for the left eye would indicate that only one quarter (9) of the target lights were seen with the left eye.

Ten patients were tested on two occasions at least one day apart, once with 0.1% oxymetazoline, and another time with Visine® L.R.®. A total of 14 eyes were tested. In nine of the patients, 0.1% oxymetazoline was placed in one eye (or both eyes) on a given day, and Visine® L.R.® was placed in the same eye(s) on a separate day. One patient had Visine® L.R.® in one eye and 0.1% oxymetazoline in the other eye on a first day, then Visine® L.R.® and 0.1% oxymetazoline in the opposite eyes on a second day.

Figure 3A:
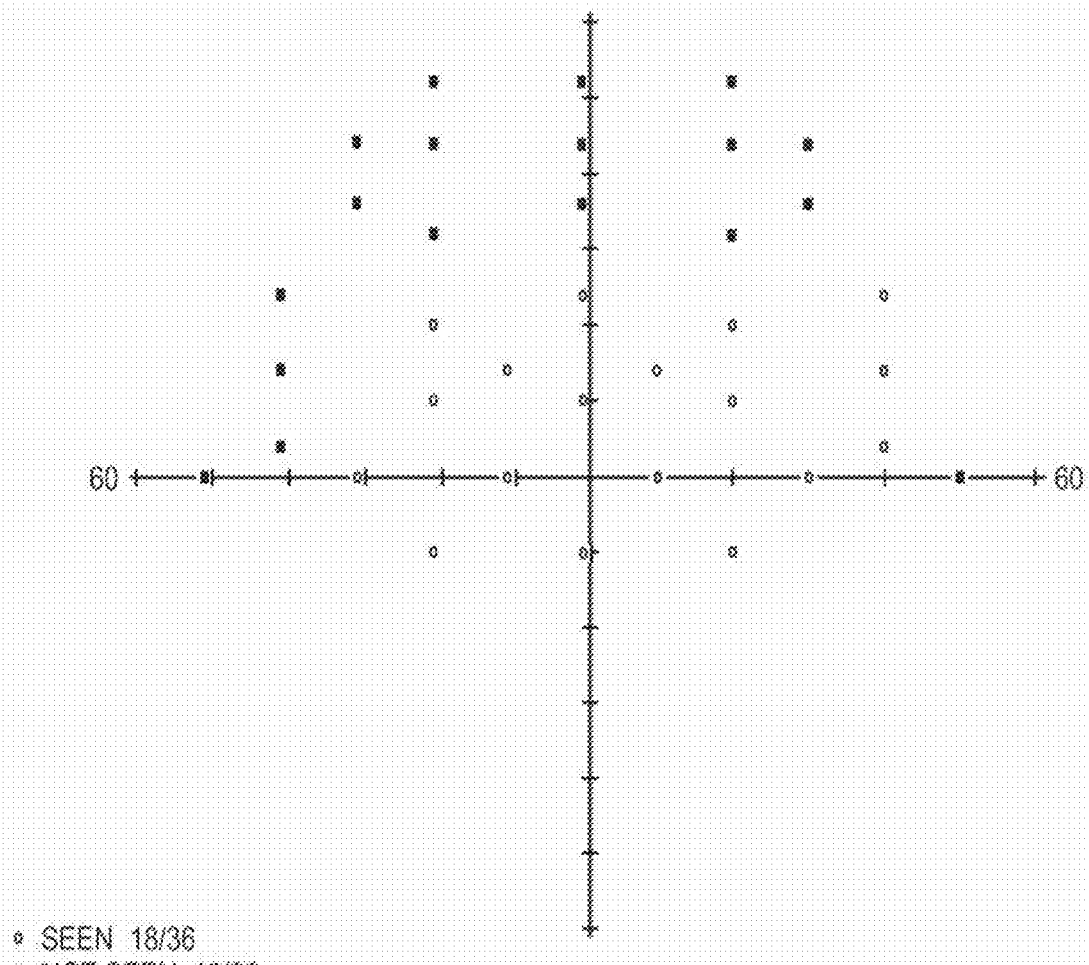
FIG. 3A is a baseline visual field map of a ptotic eye in a patient with significant ptosis of one eye. Open ovals represent seen spots. Closed ovals represent not seen spots.
Figure 3B:
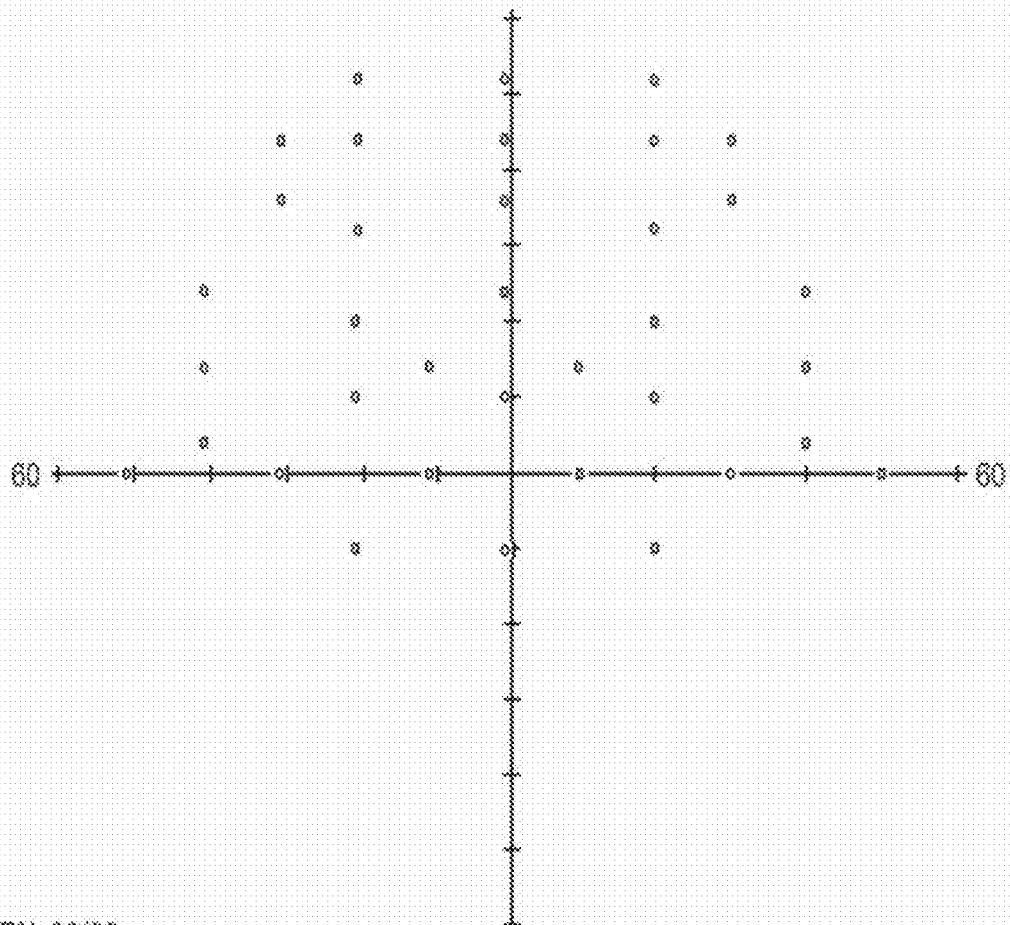
FIG. 3B is a visual field map of the same ptotic eye as in FIG. 3A, measured 2 hours and 20 minutes following administration of a single drop of 0.1% oxymetazoline to that eye.
Figure 3C:
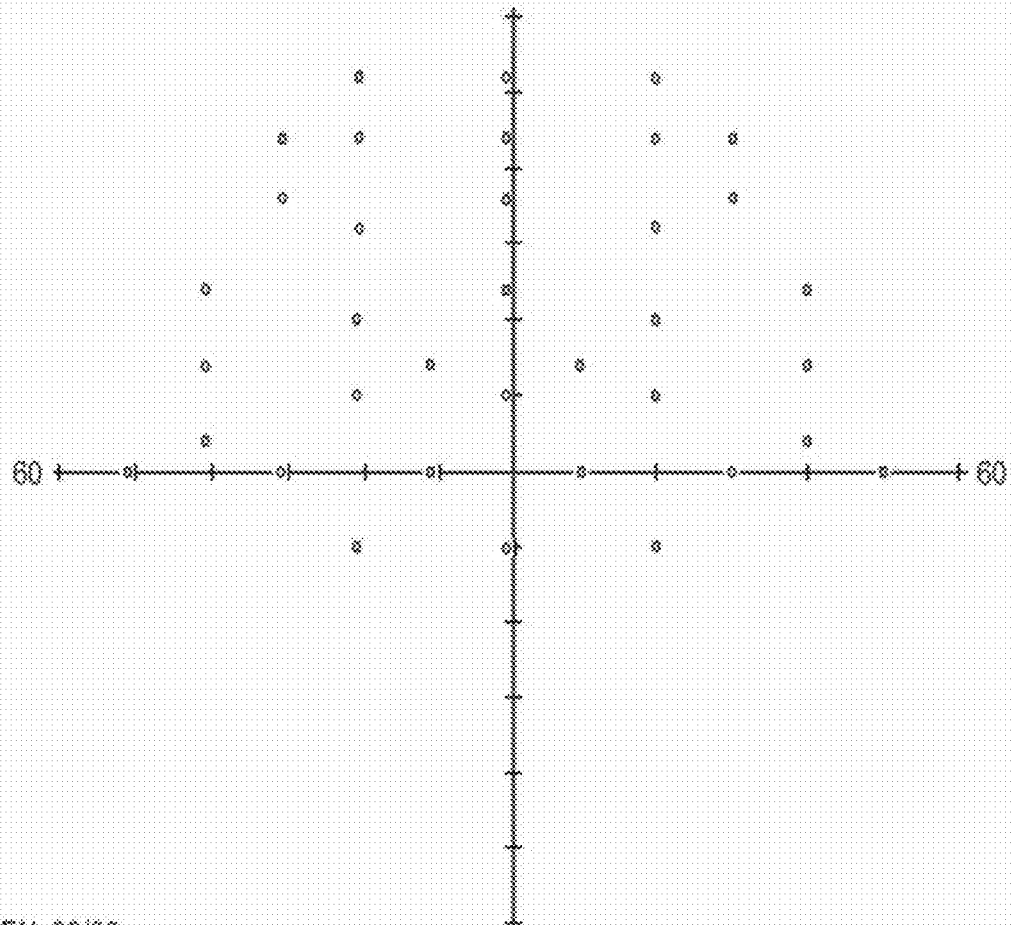
FIG. 3C is a visual field map of the same ptotic eye as in FIG. 3A and FIG. 3B, measured 4 hours following administration of a single drop of 0.1% oxymetazoline to that eye.

Fields were measured before and after administration of drops. Results are shown in Table 7, and representative maps are shown in FIG. 3A-C. Visual field tests were performed serially at different times following administration. The results in Table 7 represent the "best" results.

TABLE 7

Effects of 0.1% Oxymetazoline and Visine ® L.R. ® on Visual Field 0.1% Oxymetazoline

| | | Baseline (%) | | After Rx (%) | | Δ % | |
|---|---|---|---|---|---|---|---|
| Patient | Rx | OD | OS | OD | OS | OD | OS |
| 34 | OS | 50 | 42 | 50 | 56 | 0 | 14 |
| 35 | OD | 50 | 94 | 100 | 100 | 50 | 6 |
| 36 | OU | 53 | 39 | 92 | 81 | 39 | 42 |
| 37 | OS | 83 | 61 | 100 | 97 | 17 | 36 |
| 38 | OU | 22 | 25 | 67 | 72 | 45 | 47 |
| 39 | OS | 81 | 61 | 100 | 100 | 19 | 39 |
| 40 | OS | 69 | 19 | 72 | 47 | 3 | 28 |
| 41 | OS | 94 | 53 | 100 | 69 | 6 | 16 |
| 42 | OU | 50 | 33 | 81 | 81 | 31 | 48 |
| 43 | OS | 78 | 75 | 97 | 100 | 19 | 25 |
| 43 | OD | 69 | 81 | 94 | 69 | 25 | −12 |

Visine ® L.R. ®

| | | Baseline (%) | | After RX (%) | | Δ (%) | |
|---|---|---|---|---|---|---|---|
| Patient | Rx | OD | OS | OD | OS | OD | OS |
| 34 | OS | 53 | 47 | 50 | 53 | −3 | 6 |
| 35 | OD | 61 | 97 | 100 | 100 | 39 | 3 |
| 36 | OU | 50 | 50 | 78 | 61 | 28 | 11 |
| 37 | OS | 61 | 56 | 86 | 78 | 25 | 22 |
| 38 | OU | 17 | 25 | 19 | 31 | 2 | 6 |
| 39 | OS | 92 | 83 | 100 | 92 | 8 | 9 |
| 40 | OS | 53 | 36 | 67 | 56 | 14 | 20 |
| 41 | OS | 94 | 56 | 94 | 64 | 0 | 8 |
| 42 | OU | 47 | 42 | 50 | 36 | 3 | −6 |
| 43 | OS | 69 | 81 | 94 | 69 | 25 | −12 |
| 43 | OD | 78 | 75 | 97 | 100 | 19 | 25 |

Briefly, "negative control eyes" (i.e., those that didn't get any drop) showed 8% improvement. Eyes treated with Visine® L.R. showed 11% improvement, and eyes treated with 0.1% oxymetazoline showed 35% improvement. The effect of 0.1% oxymetazoline remains striking even if adjusted by subtracting the negative control result.

Example 10

Improvement in Visual Fields with 0.1% Oxymetazoline in a Subject with Ptosis and Glaucoma A 78-year-old woman with bilateral ptosis and dense inferior visual field defects in both eyes due to glaucoma was administered a single drop of 0.1% oxymetazoline to each eye. She had essentially lost the bottom half of her vision from glaucoma (not reversible), and the top half of her vision from ptosis. Treatment with 0.1% oxymetazoline temporarily restored the top parts of her visual fields by relieving her bilateral ptosis.

EQUIVALENTS

The invention has been described broadly and generically herein. Those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention. Further, each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

INCORPORATION BY REFERENCE

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right physically to incorporate into this application any and all materials and information from any such articles, patents, patent applications, or other physical and electronic documents.

I claim:

1. A method for increasing the vertical separation of the upper and lower lids of an eye of a subject in need thereof, the method comprising:
  administering an effective amount of oxymetazoline to the exterior surface of an eye of a subject,
  wherein the oxymetazoline is formulated as a pharmaceutical composition comprising about 0.1 weight percent oxymetazoline in an ophthalmologically acceptable carrier,
  and
  wherein the subject does not have an allergic ocular condition calling for treatment of the eye with oxymetazoline, the subject does not have eyelid swelling, and the subject has not undergone refractive eye surgery.

2. The method of claim 1, wherein the administering results in at least a 5% increase in the vertical separation of the upper and lower lids of the eye.

3. The method of claim 2, wherein the administering results in at least a 10% increase in the vertical separation of the upper and lower lids of the eye.

4. The method of claim 1, wherein the administering results in at least a 0.5 mm increase in the vertical separation of the upper and lower lids of the eye.

5. The method of claim 1, wherein the administering results in at least a 1 mm increase in the vertical separation of the upper and lower lids of the eye.

6. The method of claim 1, wherein the oxymetazoline is provided as a pharmaceutically acceptable salt of oxymetazoline.

7. The method of claim 1, wherein the oxymetazoline is administered as a single drop.

8. The method of claim 1, wherein the oxymetazoline is administered either once daily or at least once a day.

9. A method for increasing the vertical separation of the upper and lower lids of an eye of a subject in need thereof, the method comprising:
   administering to the exterior surface of an eye of a subject an effective amount of a composition comprising about 0.1 weight percent oxymetazoline in an ophthalmologically acceptable carrier,
   wherein the subject does not have an allergic ocular condition calling for treatment of the eye with oxymetazoline, the subject does not have eyelid swelling, and the subject has not undergone refractive eye surgery.

* * * * *